United States Patent
Ortiz (10) Patent No.: US 7,766,815 B2
(45) Date of Patent: Aug. 3, 2010

(54) ELECTROACTIVE POLYMER ACTUATED GASTRIC BAND

(75) Inventor: Mark Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1124 days.

(21) Appl. No.: 11/161,268

(22) Filed: Jul. 28, 2005

(65) Prior Publication Data

US 2007/0027356 A1    Feb. 1, 2007

(51) Int. Cl.
    *A61F 2/00*     (2006.01)
    *A61B 17/08*     (2006.01)

(52) U.S. Cl. .......... 600/37; 606/151

(58) Field of Classification Search .......... 600/37, 600/30, 593; 606/157, 151, 158; 36/50.5; 24/16 PB, 30.5 R, 30.5 L, 70 SK; 128/899; A61B 17/08, A61B 19/00
See application file for complete search history.

(56) References Cited

U.S. PATENT DOCUMENTS

| | | | |
|---|---|---|---|
| 3,860,997 A * | 1/1975 | Van Riper et al. .......... 24/16 PB |
| 4,592,339 A | 6/1986 | Kuzmak et al. | |
| 5,074,868 A | 12/1991 | Kuzmak | |
| 5,087,852 A * | 2/1992 | Culp .......... 310/323.06 |
| 5,226,429 A | 7/1993 | Kuzmak | |
| 5,449,368 A | 9/1995 | Kuzmak | |
| 5,526,555 A * | 6/1996 | Battistella et al. .......... 24/68 SK |
| 5,601,604 A | 2/1997 | Vincent | |
| 5,771,903 A | 6/1998 | Jakobsson | |
| 5,910,149 A | 6/1999 | Kuzmak | |
| D413,197 S * | 8/1999 | Faye .......... D2/978 |
| 6,102,922 A | 8/2000 | Jakobsson et al. | |
| 6,185,791 B1 * | 2/2001 | Khokhar .......... 24/16 PB |
| 6,210,347 B1 * | 4/2001 | Forsell .......... 600/593 |
| 6,249,076 B1 * | 6/2001 | Madden et al. .......... 310/363 |
| 6,511,490 B2 | 1/2003 | Robert | |
| 6,676,674 B1 | 1/2004 | Dudai | |
| 6,694,982 B2 | 2/2004 | Latour | |
| 6,749,556 B2 * | 6/2004 | Banik .......... 600/30 |
| 7,013,538 B2 * | 3/2006 | Browne et al. .......... 24/603 |
| 2002/0198548 A1 | 12/2002 | Robert | |
| 2003/0088948 A1 * | 5/2003 | Cook .......... 24/16 PB |
| 2003/0120288 A1 | 6/2003 | Benchetrit | |
| 2003/0139808 A1 * | 7/2003 | Shahinpoor et al. .......... 623/4.1 |

(Continued)

FOREIGN PATENT DOCUMENTS

CN     1618411 A     5/2005

(Continued)

OTHER PUBLICATIONS

Chinese Office Action for Application No. 200610108908.X dated Jul. 3, 2009.

*Primary Examiner*—Charles A Marmor, II
*Assistant Examiner*—Catherine E Burk (57) ABSTRACT

Methods and devices are provided for remotely adjusting a size of a gastric band disposed around a patient's stomach. In one exemplary embodiment, a gastric band is provided having a first end and a second end that mate to one another to encircle a stomach. A latch mechanism can be formed on the band, and at least one actuator can be coupled to the latch mechanism and it can be adapted to expand and contract the latch mechanism when energy is applied thereto to adjust a diameter of the band. In one exemplary embodiment, the actuator(s) is an electroactive polymer actuator.

16 Claims, 6 Drawing Sheets

U.S. PATENT DOCUMENTS

| | | |
|---|---|---|
| 2003/0158564 A1 | 8/2003 | Benchetrit |
| 2004/0049209 A1 | 3/2004 | Benchetrit |
| 2004/0089313 A1 | 5/2004 | Utley et al. |
| 2004/0133219 A1* | 7/2004 | Forsell ............... 606/151 |
| 2004/0153106 A1 | 8/2004 | Dudai |
| 2004/0158272 A1 | 8/2004 | Hofle et al. |
| 2004/0173219 A1* | 9/2004 | Bakane ............... 128/885 |
| 2004/0230137 A1 | 11/2004 | Mouton |
| 2004/0249453 A1 | 12/2004 | Cartledge et al. |
| 2004/0267291 A1 | 12/2004 | Byrum et al. |
| 2005/0002984 A1 | 1/2005 | Byrum et al. |
| 2006/0173238 A1* | 8/2006 | Starkebaum ............... 600/37 |
| 2006/0199997 A1* | 9/2006 | Hassler et al. ............... 600/37 |
| 2006/0211912 A1* | 9/2006 | Dlugos et al. ............... 600/37 |
| 2006/0252982 A1* | 11/2006 | Hassler et al. ............... 600/37 |

FOREIGN PATENT DOCUMENTS

| | | |
|---|---|---|
| EP | 0611561 | 2/1993 |
| EP | 0702529 | 5/1993 |
| EP | 0769282 | 4/1997 |
| EP | 1036545 | 3/1999 |
| EP | 1091707 | 1/2000 |
| EP | 1205148 | 5/2002 |
| EP | 1319371 | 11/2002 |
| EP | 1396242 | 3/2004 |
| EP | 1484040 | 12/2004 |
| EP | 1491168 | 12/2004 |
| EP | 1547549 | 6/2005 |
| NO | 161242 | 9/1985 |
| WO | WO 86/04498 | 2/1985 |
| WO | WO-92/02182 | 8/1990 |
| WO | WO-98/56321 | 6/1997 |
| WO | WO 01/41671 | 11/1999 |
| WO | WO 01/45597 | 12/1999 |
| WO | WO 01/52777 | 1/2000 |
| WO | WO 01/85071 | 5/2000 |
| WO | WO 01/19297 | 3/2001 |
| WO | WO 01/24742 | 4/2001 |
| WO | WO 02/096326 | 12/2002 |
| WO | WO 03/057090 | 7/2003 |
| WO | WO 03/057091 | 7/2003 |
| WO | WO 03/057092 | 7/2003 |
| WO | WO 03/059215 | 7/2003 |
| WO | WO-2004/105622 | 12/2004 |

* cited by examiner

ELECTROACTIVE POLYMER ACTUATED GASTRIC BAND

FIELD OF THE INVENTION

The present invention relates broadly to bariatric devices, and in particular to methods and devices for remotely adjusting a diameter of a gastric band.

BACKGROUND OF THE INVENTION

Obesity is an increasing common problem among people of all ages, resulting in numerous health problems, such as diabetes and heart disease. One solution for combating obesity is gastric band surgery, in which a constricting ring or band is placed around the top of the stomach near the esophagus to limit the patient's food intake. Originally, the insertion of a gastric band required major surgery which included a large incision in the patient's abdomen. An improvement on this approach was the introduction of gastric bands that can be implanted laparoscopically. Using a laparoscopic approach, only small incisions are made through which surgical instruments are passed to insert the gastric band around the stomach, reducing the size of the incision and decreasing the amount of potential tissue damage.

While the original gastric bands could only be adjusted through a subsequent surgery, adjustable bands have been developed that allow a surgeon to adjust the diameter of the band depending on the needs of the patient without an invasive procedure. In some current models of adjustable bands, a band with an inflatable balloon is used. This inflatable balloon is connected through tubing to a port placed under the patient's skin. Using needles inserted into the port, saline is passed through the tubing to inflate or deflate the balloon to decrease or increase the size of the bands diameter, thus controlling the food intake of the patient.

While this inflatable band eliminates the need for additional surgery to adjust the band, problems can arise through the use of the port and the needles to insert the saline. For example, repeated adjustment can cause scarring on the skin around the port. The use of a fluid-filled balloon also poses a potential risk of puncture or over-inflation.

Accordingly, there is a need for improved methods and devices for adjusting the size of a gastric band after it is implanted.

BRIEF SUMMARY OF THE INVENTION

The present invention generally provides methods and devices for remotely actuating a gastric band to adjust a diameter thereof. While this can be achieved using a variety of techniques, in one embodiment the device can include a flexible band having a first end and a second end that mate to one another to encircle a stomach. At least one actuator can be coupled to the flexible band and it can be adapted to expand and contract when electrical energy is applied thereto to adjust a diameter of the band. In one exemplary embodiment, the actuator(s) can be coupled to a latch mechanism formed on the band, and it can be adapted to expand and contract the latch mechanism when electrical energy is applied thereto to adjust a diameter of the band.

While the band and the latch mechanism can each have a variety of configurations, in one exemplary embodiment the band can include teeth formed on the first end and the latch mechanism can be formed on the second end and it can be configured to engage the teeth. In particular, the latch mechanism can include a traversing actuator that is adapted to engage the teeth to selectively move the first and second ends relative to one another, thus allowing a diameter of the band to be decreased. While the actuator(s) can be coupled to the latch mechanism in a variety of orientations to form a traversing actuator, in one exemplary embodiment the traversing actuator can be coupled to a first flexible arm extending from the latch mechanism and adapted to engage one of the teeth. In use, when energy is delivered to the traversing actuator, the traversing actuator can be adapted to expand the first arm to move from engagement with a first tooth to engagement with a second tooth. When the energy delivery is terminated, the traversing actuator contracts the first arm to move the second end of the band relative to the first end of the band, thereby decreasing a diameter of the flexible band. In a further embodiment, at least one additional arm can be positioned adjacent to the first arm for maintaining engagement with the first tooth while the first arm is expanded to engage a second tooth.

In another embodiment, the latch mechanism can include a locking actuator that is adapted to releasably lock the first and second ends of the band relative to one another. The locking actuator can be adapted to increase an opening within the latch mechanism when energy is delivered thereto to allow slidable movement of the first and second ends relative to one another. Thus, when the locking actuator is activated to release the first and second ends, the first and second ends can slide relative to one another to allow a diameter of the band to increase. While the actuator(s) can be coupled to the latch mechanism in a variety of orientations to form a locking actuator, in one exemplary embodiment the latch mechanism can be in the form of a housing having an opening formed therethrough and defined by opposed first and second sidewalls and top and bottom surfaces extending between the first and second side walls. The locking actuator can include a first actuator coupled to the first sidewall and a second actuator coupled to the second sidewall. When energy is delivered to the first and second actuators, the actuators can increase the height of the first and second sidewalls, thereby increasing the opening to allow slidable movement of the first and second ends of the gastric band. The gastric band can also optionally include a biasing element to bias the band to a maximum diameter when the locking actuator is activated. One suitable biasing element is, by way of non-limiting example, a spring formed on an inner perimeter of the band.

The actuator(s) can be formed from a variety of materials. In one exemplary embodiment, the actuator(s) can be in the form of an electroactive polymer (EAP). For example, the actuator(s) can be in the form of a fiber bundle having a flexible conductive outer shell with several electroactive polymer fibers and an ionic fluid disposed therein. Alternatively, the actuator(s) can be in the form of a laminate having at least one flexible conductive layer, an electroactive polymer layer, and an ionic gel layer. Multiple laminate layers can be used to form a composite.

Also disclosed herein are methods for remotely adjusting a gastric band disposed around a stomach. In one embodiment, the method can include selectively delivering energy to at least one electrically expandable and contractible actuator disposed on a gastric band positioned around a stomach to change a diameter of the gastric band. For example, in one embodiment, energy can be delivered to a locking actuator to allow slidable movement of first and second ends of the gastric band relative to one another, thus allowing a diameter of the band to be increased. In certain exemplary embodiments, the locking actuator can expand an opening formed in a latch mechanism on the band when energy is delivered thereto to allow slidable movement of the first and second ends of the band. In another embodiment, energy can be delivered to a traversing actuator to move first and second ends of the band relative to one another, thus allowing a diameter of the band to be decreased. In certain exemplary embodiments, the first end of the band can include teeth formed thereon, and the second end can include a latch mechanism formed thereon and having an arm extending therefrom for engaging at least one of the teeth. When energy is delivered to the traversing actuator, the arm can expand to engage an adjacent tooth. When energy delivery is terminated, the arm can contract to move the first and second ends relative to one another and decrease a diameter of the band. While energy can be delivered using a variety of techniques, in one exemplary embodiment energy is delivered remotely to a subcutaneous transformer that is coupled to the electrically expandable and contractible actuator(s).

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

Figure 1A:
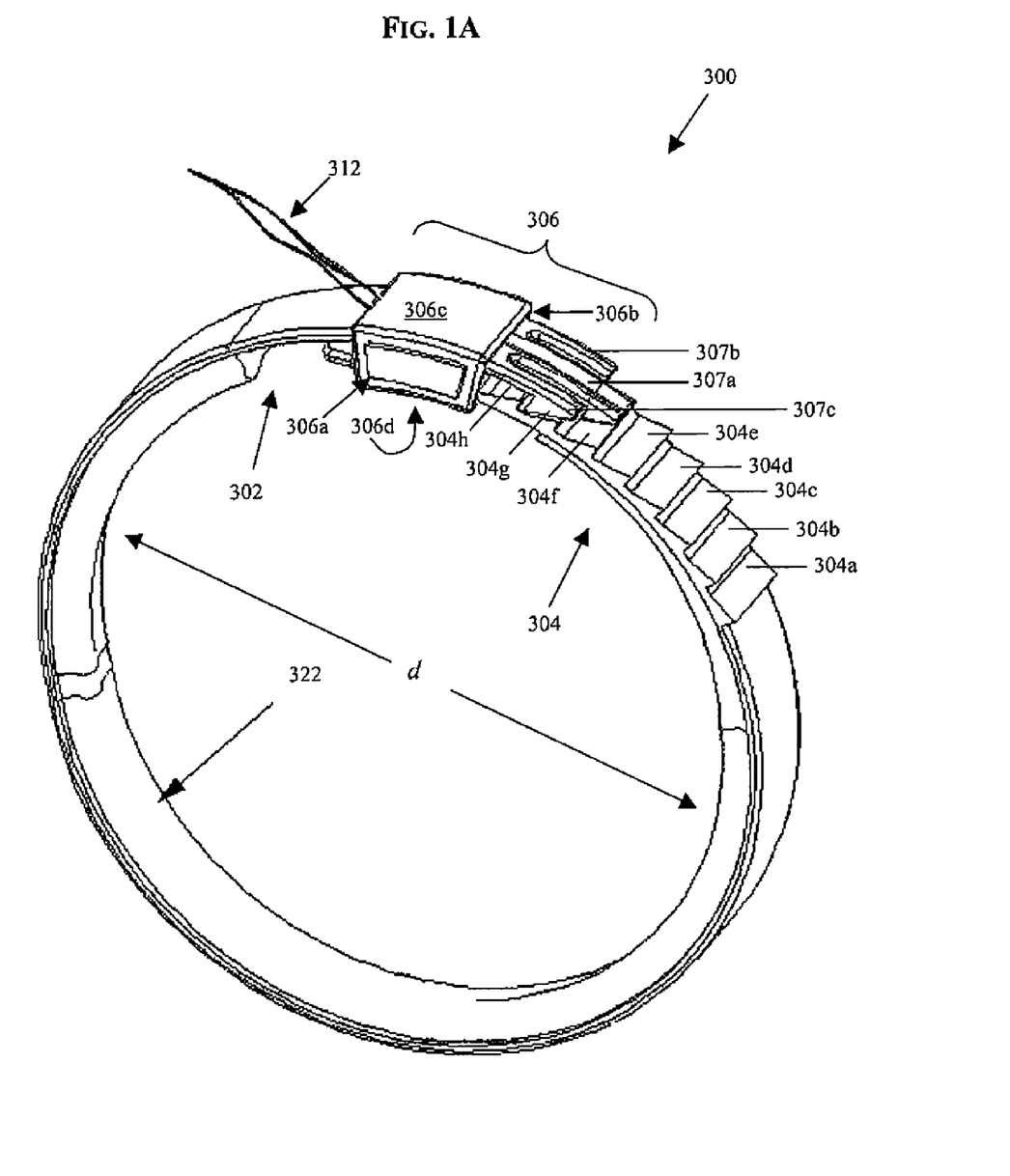
FIG. 1A is a perspective view of one exemplary embodiment of an adjustable gastric band.
Figure 1B:
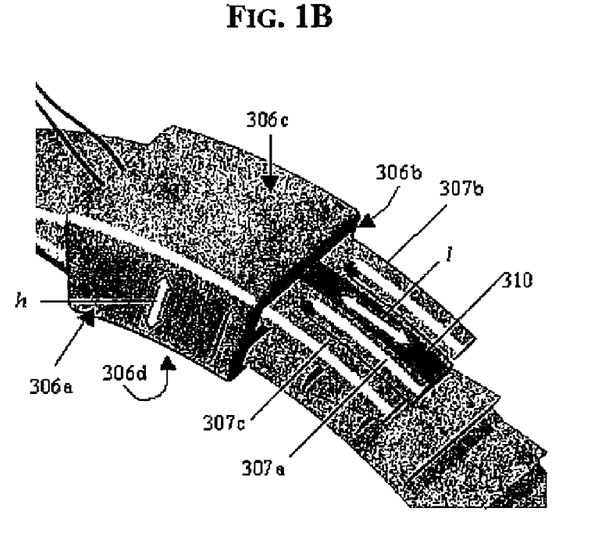
FIG. 1B is a perspective view of the latch mechanism and actuators of the gastric band shown in FIG. 1A.
Figure 1C:
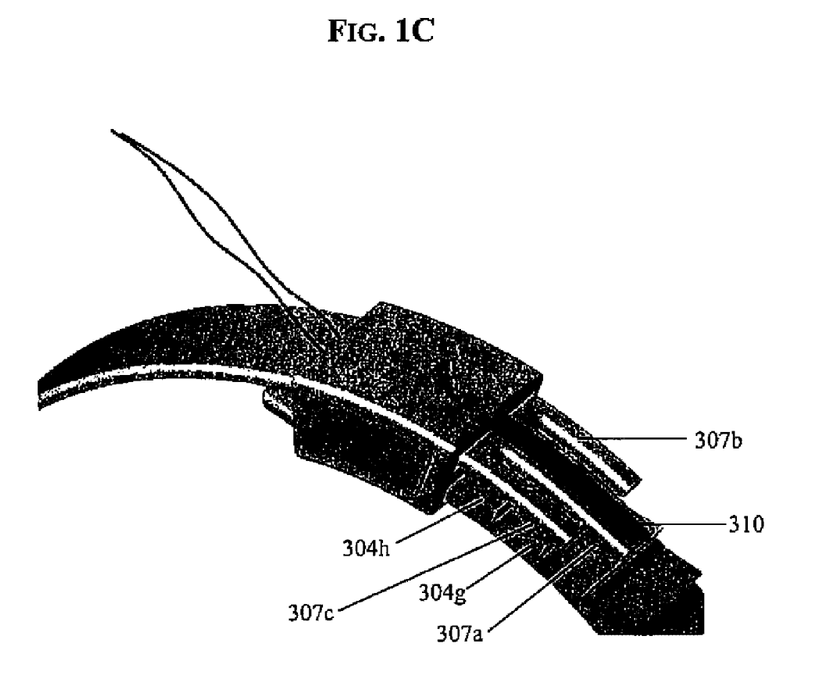
FIG. 1C is a perspective view of the latch mechanism and actuators shown in FIG. 1B, showing a traversing actuator activated and in an expanded configuration.

The present invention generally provides methods and devices for remotely adjusting a diameter of a gastric band. While the gastric band can have virtually any configuration, and the various techniques for remotely adjusting a diameter of a gastric band can be incorporated into any gastric band or similar device known in the art, FIGS. 1A-1C illustrate one exemplary embodiment of a gastric band. As shown, the gastric band 300 has a generally elongate shape with opposed ends 302, 304, referred to herein as a head 302 and a tail 304, that mate to one another to form a loop. The diameter d of the band 300 can vary, but in an exemplary embodiment it is preferably sized to fit around a stomach for use in treating obesity. The band 300 can also be formed from a variety of materials, but in one exemplary embodiment it is preferably flexible to allow the diameter d of the band 300 to vary. The band 300 can also include other features to facilitate use. For example, an inner surface of the band 300 can be formed from a material that is amendable to tissue contact. By way of non-limiting example, the inner surface of the band 300 can include an inflatable balloon 322, as shown, disposed therearound to provide a relatively soft surface for contacting the stomach.

The head 302 and the tail 304 of the band 300 can each have a variety of configurations, and various techniques can be used to mate the head 302 and tail 304. In the illustrated exemplary embodiment, the tail 304 has several teeth 304a-h formed thereon, and the head 302 has a latch mechanism 306 formed thereon for receiving the tail 304 and engaging the teeth 304a-h. While the shape and size of the latch mechanism 306 can vary, in one exemplary embodiment the latch mechanism 306 can be in the form of a substantially rectangular housing having opposed first and second sidewalls 306a, 306b and top and bottom surfaces 306c, 306d extending between the first and second sidewalls 306a, 306b. The sidewalls 306a, 306b and top and bottom surfaces 306c, 306d can define an opening formed therethrough for receiving the tail 304 of the band 300. In order to facilitate adjustment of a diameter d of the band 300, at least a portion of the housing, and more preferably the sidewalls 306a, 306b of the housing, can be formed from a flexible and/or elastic material to allow the sidewalls 306a, 306b to expand and contract to increase and decrease a size of the opening, thereby allow a diameter d of the band 300 to be adjusted, as will be discussed in more detail below. By way of non-limiting example, in an exemplary embodiment the flexible and/or elastic latch mechanism is formed from a biocompatible polymer, such as silicone or latex. Other suitable biocompatible elastomers include, by way of non-limiting example, synthetic polyisoprene, chloroprene, fluoroelastomer, nitrile, and fluorosilicone. A person skilled in the art will appreciate that the materials can be selected to obtain the desired mechanical properties.

The latch mechanism 306 can also include one or more arms formed thereon for engaging one or more of the teeth 304a-h on the tail 304. In the embodiment shown in FIG. 1A, the latch mechanism 306 has a central arm 307a and opposed side arms 307b, 307c formed on each side of the central arm 307a. Each arm 307a, 307b, 307c can have a variety of shapes and size, and the configuration can vary depending on the configuration of the teeth 304a-h formed on the tail 304. In the illustrated exemplary embodiment, each arm 307a, 307b, 307c extends from the top surface 306a of the housing and has a generally elongate shape with a hook-shaped member formed on a terminal end thereof and in facing relationship with the teeth 304a-h. The hook-shaped member on each arm 30a7, 307b, 307c can extend at an angle that complements an angle of the teeth 304a-h to allow the arms 30a7, 307b, 307c to engage the teeth 304a-h and prevent the band 300 from opening. In order to facilitate adjustment of a diameter d of the band 300, at least one of the arms, e.g., the central arm 307a, can be formed from a flexible and/or elastic material to allow the arm 307a to expand and contract to engage adjacent teeth and thereby adjust a diameter of the band 300, as will be discussed in more detail below. A person skilled in the art will appreciate that a flexible and/or elastic arm 307a can be formed using a variety of materials, such as those materials previously mentioned.

As previously indicated, the latch mechanism 306 can also include at least one actuator coupled thereto for adjusting the diameter d of the band 300. While the number of actuators can vary, in one exemplary embodiment the latch mechanism 306 can include a locking actuator and a traversing actuator. The locking actuator can be adapted to lock the head and tail 302, 304 to one another when in a resting configuration, and to unlock the head and tail 302, 304 when energy is delivered thereto. As a result, when the locking actuator is activated, the head and tail 302, 304 can slide freely relative to one another, thus allowing the diameter d of the band 300 to be increased. As will be discussed in more detail below, the band 300 can include a biasing element to bias the band 300 to a maximum diameter, thereby increasing the diameter d when the locking actuator 308 is activated. The traversing actuator can be adapted to move the head and tail 302, 304 relative to one another when energy is delivered to the traversing actuator, thereby allowing the diameter d of the band 300 to be decreased.

While the actuators can have a variety of configurations, one suitable configuration is an electroactive polymer actuator. Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired with some form of ionic fluid or gel using electrodes. Upon application of a voltage potential to the electrodes, a flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect of the EAP on the mechanical mechanism when voltage is applied to the EAP. The amount of voltage delivered to the EAP can also correspond to the amount of movement or change in dimension that occurs, and thus energy delivery can be controlled to effect a desired amount of change.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long strands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. An example of a commercially available fiber EAP material is manufactured by Santa Fe Science and Technology and sold as PANION™ fiber and described in U.S. Pat. No. 6,667,825, which is hereby incorporated by reference in its entirety.

Figure 2A:
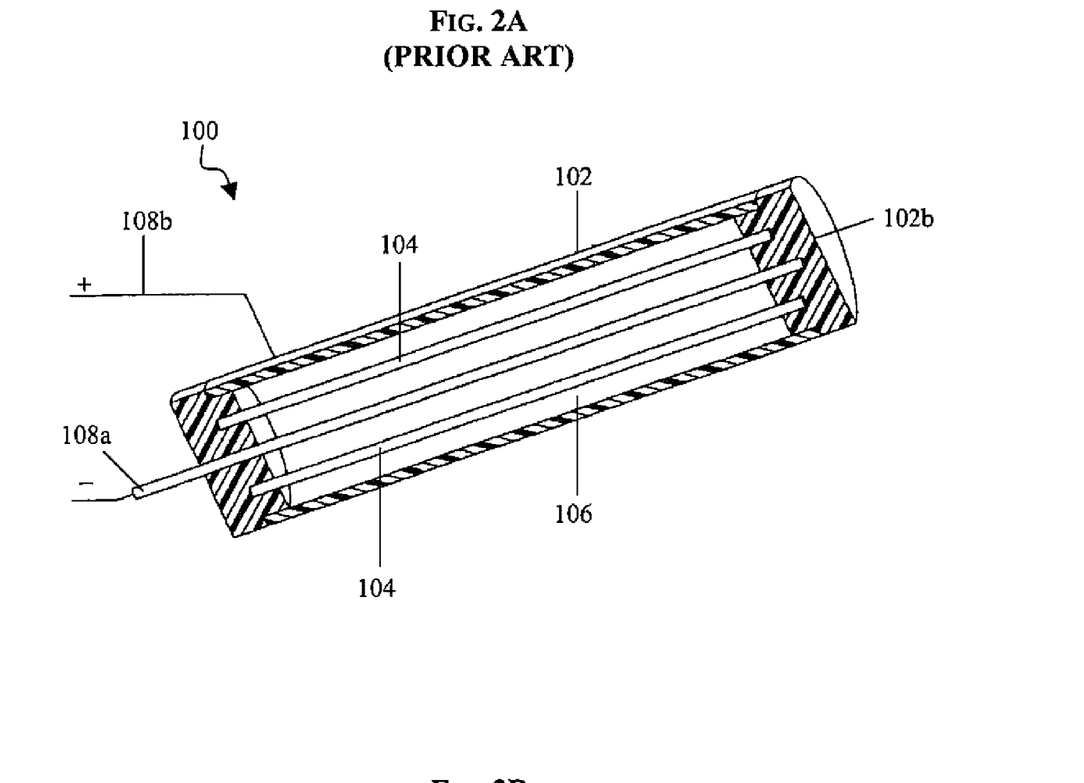
FIG. 2A is a cross-sectional view of a prior art fiber bundle type EAP actuator.
Figure 2B:
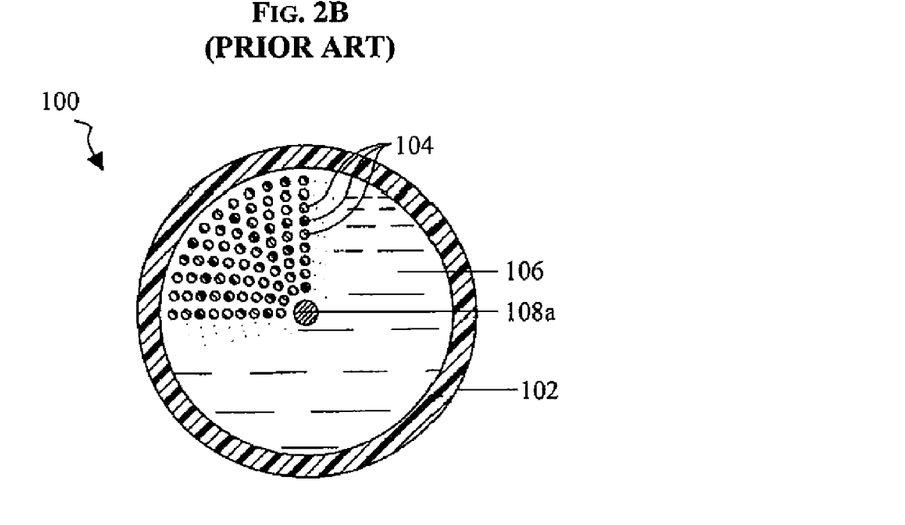
FIG. 2B is a radial cross-sectional view of the prior art actuator shown in FIG. 2A.

FIGS. 2A and 2B illustrate one exemplary embodiment of an EAP actuator 100 formed from a fiber bundle. As shown, the actuator 100 generally includes a flexible conductive outer sheath 102 that is in the form of an elongate cylindrical member having opposed insulative end caps 102a, 102b formed thereon. The conductive outer sheath 102 can, however, have a variety of other shapes and sizes depending on the intended use. As is further shown, the conductive outer sheath 102 is coupled to a return electrode 108a, and an energy delivering electrode 108b extends through one of the insulative end caps, e.g., end cap 102a, through the inner lumen of the conductive outer sheath 102, and into the opposed insulative end cap, e.g., end cap 102b. The energy delivering electrode 108b can be, for example, a platinum cathode wire. The conductive outer sheath 102 can also include an ionic fluid or gel 106 disposed therein for transferring energy from the energy delivering electrode 108b to the EAP fibers 104, which are disposed within the outer sheath 102. In particular, several EAP fibers 104 are arranged in parallel and extend between and into each end cap 102a, 120b. As noted above, the fibers 104 can be arranged in various orientations to provide a desired outcome, e.g., radial expansion or contraction, or bending movement. In use, energy can be delivered to the actuator 100 through the active energy delivery electrode 108b and the conductive outer sheath 102 (anode). The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 120b will be pulled toward one another, thereby contracting and decreasing the length of the flexible outer sheath 102.

Another type of EAP is a laminate structure, which consists of one or more layers of an EAP, a layer of ionic gel or fluid disposed between each layer of EAP, and one or more flexible conductive plates attached to the structure, such as a positive plate electrode and a negative plate electrode. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 3A:
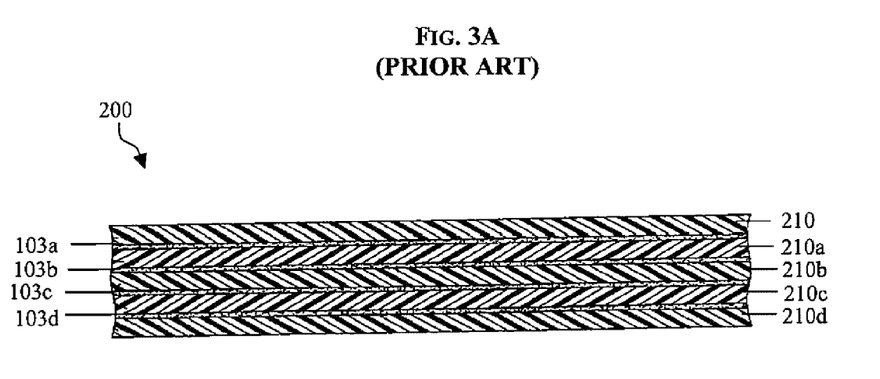
FIG. 3A is a cross-sectional view of a prior art laminate type EAP actuator having multiple EAP composite layers.
Figure 3B:
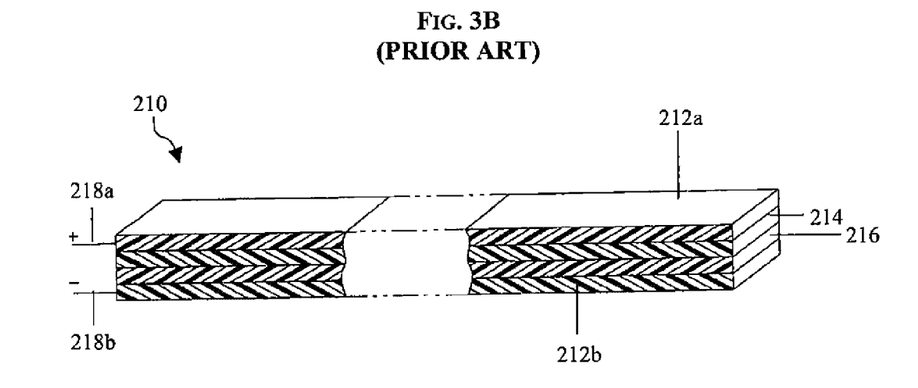
FIG. 3B is a perspective view of one of the composite layers of the prior art actuator shown in FIG. 3A.

FIGS. 3A and 3B illustrate an exemplary configuration of an EAP actuator 200 formed from a laminate. Referring first to FIG. 3A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 3B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 3B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Referring back to FIG. 1A, as previously discussed the gastric band 300 can include a locking actuator and/or a traversing actuator. Exemplary configurations of each actuator are shown in more detail in FIGS. 1B and 1C, however a person skilled in the art will appreciate that a variety of other techniques can be used to form locking and/or traversing actuators.

As shown, one exemplary locking actuator can be formed by coupling a first actuator 308 to the first sidewall 306a of the housing portion of the latch mechanism 306, and coupling a second actuator (not shown) to the second sidewall 306b of the housing portion of the latch mechanism 306. The locking actuators 308 can be coupled to the sidewalls 306a, 306b using a variety of techniques, and they can optionally form the sidewalls 306a, 206b, be embedded within the sidewalls 306a, 306b, or disposed on the sidewalls 306a, 306b. In the illustrated embodiment the locking actuators 308 are adhered to an external surface of each sidewall 306a, 306b. The orientation of the locking actuators 308 can also vary depending on the type of actuator used, but in the illustrated exemplary embodiment the locking actuators 308 are in the form of elongate bands or sheets formed from an EAP laminate, or an EAP composite formed from multiple laminates. The bands or sheets can be oriented to expand in the direction of the top and bottom surfaces 306c, 306d (which will result in contraction in a transverse direction). As a result, when energy is delivered to the actuators 308, the actuators 308 expand to increase a height of the housing, thereby increasing the size of the opening within latch mechanism 306 to allow slidable movement of the first and second ends 302, 304 of the band 300 relative to one another. In particular, increasing the opening removes the downward force applied by the latch mechanism 306 to the tail 304, allowing the arms 307a, 307b, 307c of the latch mechanism 306 to disengage from the teeth 304a-h on the tail 304, thereby causing the head 302 and the tail 304 to separate and slide apart to increase the diameter d of the band 300. When energy delivery to the locking actuator 308 is terminated, the height h of the first and second sidewalls 306a, 306b decreases to their original height, thereby decreasing the opening to its original size and returning the downward force from the latch mechanism 306 onto the tail 304 to lock the head 302 and tail 304 together.

Figure 4:
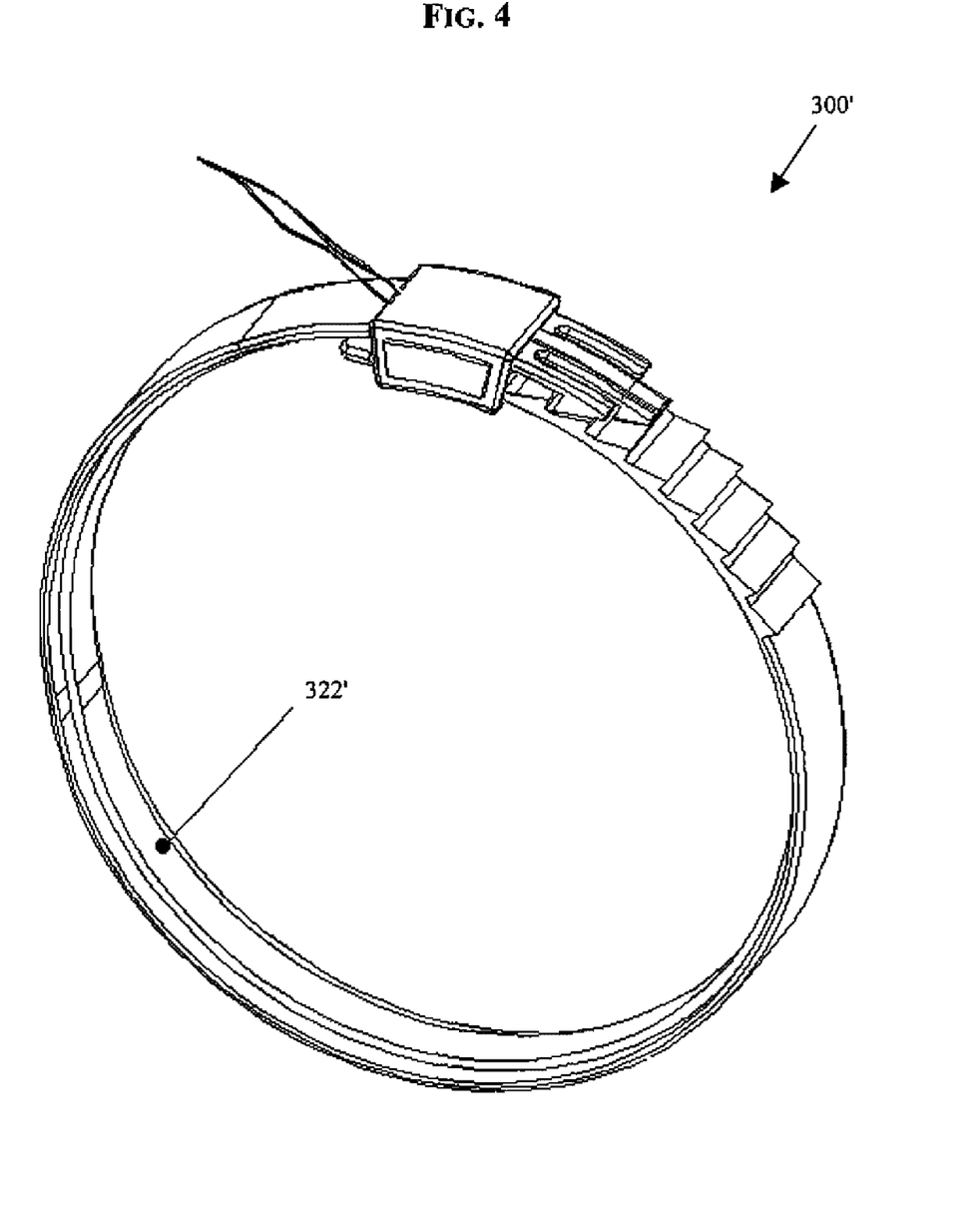
FIG. 4 is a perspective view of another exemplary embodiment of a remotely adjustable gastric band.

As previously indicated, in order to facilitate opening of the band 300 when the locking actuator 308 is activated, the band can include a biasing element for biasing the band 300 to a maximum diameter. While the biasing element can have a variety of configurations, in one exemplary embodiment, shown in FIG. 4, the band 300' can include a spring 322' disposed within an inner circumference thereof to bias the band 300 to a maximum diameter. A biasing element formed from an EAP actuator could also optionally be used, and energy can be delivered to the EAP actuator to bias the band open when energy is delivered to the locking actuator 308.

Referring back to FIGS. 1B and 1C, the traversing actuator can also have a variety of configurations, however in one exemplary embodiment the traversing actuator can be formed by coupling an actuator 310 to at least one of the arms, e.g., the central arm 307a, of the latch mechanism 306. The actuator 310 can be coupled to the arm 307a using a variety of techniques, but in one exemplary embodiment the actuator 310 is adhered to an external surface of the arm 307a. Alternatively, the actuator 310 can form the arm 307a or be embedded within the arm 307a. The orientation of the actuator 310 can also vary depending on the type of actuator used, but in the illustrated exemplary embodiment the actuators 310 is in the form of an elongate band formed from an EAP laminate or composite, and it is oriented to expand to increase a length l of the arm 307a (which will result in contraction in a transverse direction). As a result, when energy is delivered to the actuator 310, the central arm 307a will move from engagement with a first tooth on the tail 304 to an adjacent tooth on the tail 304. The position of arm 307a when energy is applied to traversing actuator 310 can be seen in FIG. 1C, where arm 307a is expanding and moving from tooth 304h towards adjacent tooth 304g on the tail 304. As the arm 307a expands, it can flex to move over the adjacent tooth 304g and engage the tooth 304g. The arms 307b, 307c on the sides of the central arm 307a can remain in engagement with tooth 304h to prevent the band 300 from opening. Once the central arm 307a has engaged adjacent tooth, energy delivery to the traversing actuator 310 is terminated, thereby causing the arm 307a to contract to its original length. As this contraction occurs, the side arms 307b, 307c, along with the rest of head 302 which is coupled to the latch mechanism 306, are pulled towards and flex over the adjacent tooth 304g to engage the adjacent tooth 304g, resulting in a decrease in the diameter d of the band 300. The decrease in diameter d is equal to the distance between the first tooth 304h and the adjacent tooth 304g, which can be configured to obtain a desired amount of movement. Optionally, the amount of energy delivered to the actuator 310 can be adjusted to expand the length l of the arm 307a to engage a tooth that is positioned one or more teeth apart from the tooth in current engagement with the arms 307a, 307b, 307c, thereby allowing the diameter d of the band 300 to be decreased in larger increments.

In use, after the gastric band 300 is implanted around a patient's stomach, the locking and traversing actuators 308, 310 allow the diameter of the band 300 to be selectively increased or decreased, as may be desired based on the patient's needs. As previously explained, the diameter can be decreased by delivering energy to the traversing actuator 310 to expand the arm 307a, and then terminating energy delivery to contract the arm 307a and thereby decrease the diameter of the band 300. This can be repeated until a desired diameter is achieved. If the diameter d is too small, the locking actuator 308 can be activated to release the latch mechanism 306 and to allow the band 300 to expand to a maximum diameter. A stop mechanism can optionally be formed on the band to prevent the head and tail from becoming detached. Termination of energy delivery to the locking actuator 308 will cause the latch mechanism to re-engage the tail. The diameter can then be decreased again, if necessary.

Figure 5:
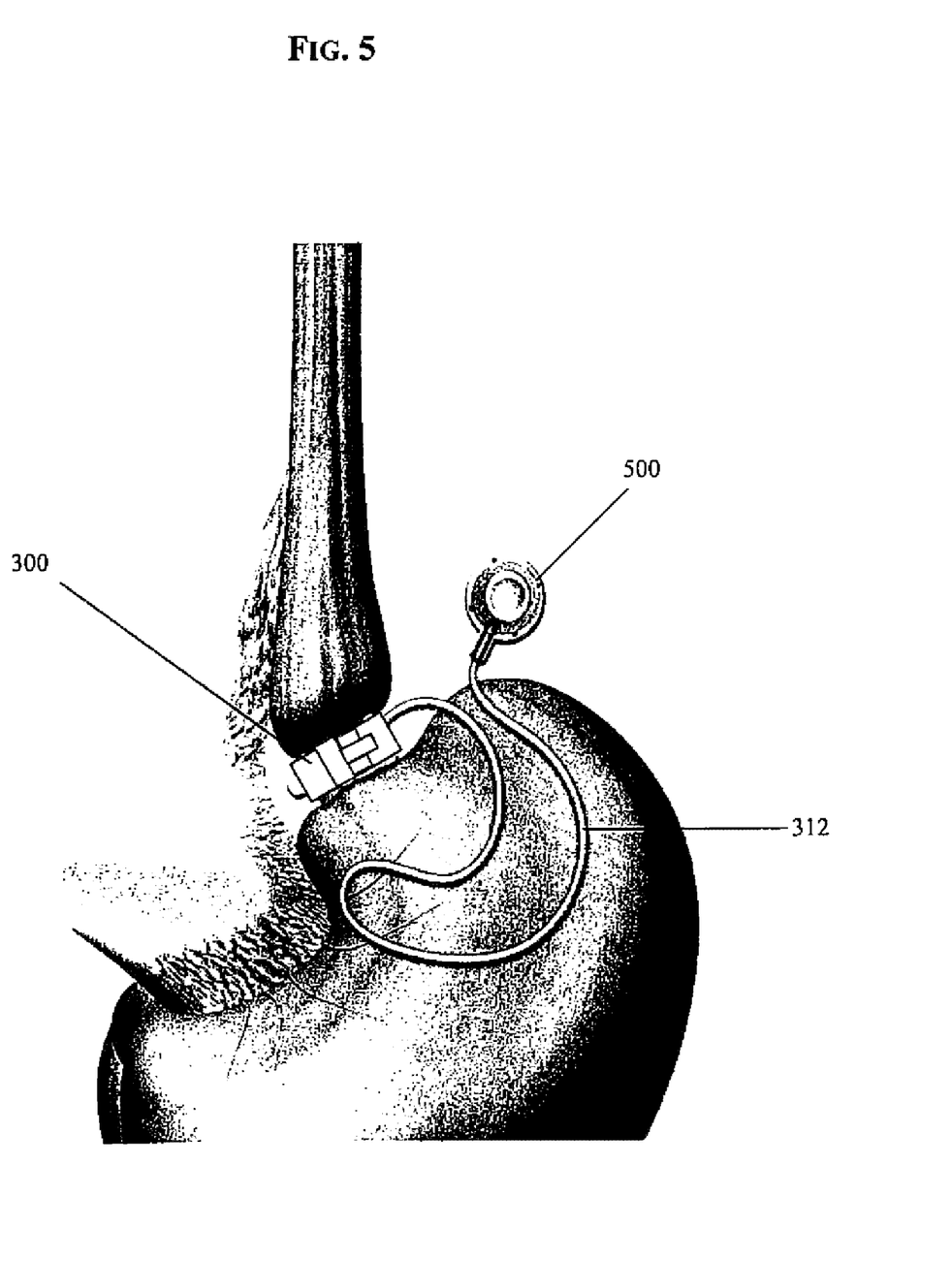
FIG. 5 is an illustration of a remotely adjustable gastric band positioned around a stomach in accordance with another exemplary embodiment.

A person skilled in the art will appreciate that a variety of techniques can be used to deliver energy to the locking and traversing actuators 308, 310, however in one exemplary embodiment each actuator 308, 310 can include a return electrode and a delivery electrode coupled thereto for separately delivering energy to each actuator 308, 310. The electrodes 312 can be coupled to a transformer that is adapted to be subcutaneously implanted and that is adapted to remotely receive energy from an external source located outside of the patient's body. This is illustrated in FIG. 5, which shows the gastric band 300 implanted around a stomach and having electrodes 312 extending therefrom and coupled to a transformer 500. Such a configuration allows the diameter d of the gastric band 300 to be adjusted without surgery.

A person skilled in the art will appreciate that a variety of other techniques can be used to adjust a diameter of a gastric band using EAPs. By way of non-limiting example, in another exemplary embodiment, EAP actuators can be placed around the entire band to allow the band to expand and contract in a radial fashion. These actuators can be coupled to an energy source that would be applied continuously to keep the band at a constant diameter. Alternatively, rather than constantly delivering energy, the actuators can be coupled to an electrical controller to time the delivery of energy on a predetermined schedule. For example, the energy delivery could be timed to vary at predetermined intervals when the patient would be consuming food to allow the diameter of the band to decrease during these time periods to limit food intake. Accordingly, the actuators can have a variety of other configurations, shapes, and sizes, and they can be positioned in a variety of orientations to provide the adjustment of the diameter of the band.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A gastric band, comprising:
   a flexible band adapted to encircle a stomach;
   a latch mechanism formed on the band, at least a portion of the latch mechanism being formed from an electroactive polymer actuator adapted to expand and contract the latch mechanism when energy is applied thereto to adjust a diameter of the band;
   wherein the flexible band includes a first end with a plurality of teeth formed thereon, and a second end having the latch mechanism formed therein for engaging the plurality of teeth formed on the first end;
   wherein the latch mechanism includes a locking actuator formed from an electroactive polymer and adapted to releasably lock the first and second ends relative to one another, and a traversing actuator formed from an electroactive polymer adapted to engage the teeth to selectively move the first and second ends relative to one another.

2. The device of claim 1, wherein the locking actuator is adapted to increase an opening within the latch mechanism when energy is delivered thereto to allow slidable movement of the first and second ends relative to one another.

3. The device of claim 2, wherein the opening in the latch mechanism is defined by a housing having opposed first and second sidewalls and top and bottom surfaces extending between the first and second side walls and wherein the locking actuator comprises a first electroactive polymer actuator coupled to the first sidewall and a second electroactive actuator coupled to the second sidewall.

4. The device of claim 3, wherein the first and second electroactive polymer actuators are adapted to increase a height of the first and second sidewalls.

5. The device of claim 1, wherein the traversing actuator is coupled to a first arm extending from the latch mechanism and adapted to engage one of the plurality of teeth.

6. The device of claim 5, wherein the traversing actuator is adapted to expand the first arm to move from engagement with a first tooth to engagement with a second tooth when energy is delivered to the traversing actuator, and to contact the first arm to move the second end relative to the first end to decrease a diameter of the flexible band when energy delivery is terminated.

7. The device of claim 6, further comprising at least one additional arm positioned adjacent to the first arm and adapted to maintain engagement with the first tooth while the first arm is expanded to engage a second tooth.

8. The device of claim 1, wherein the electroactive polymer actuator is coupled to a transformer that is adapted to be subcutaneously implanted and to remotely receive energy from an external energy source.

9. The device of claim 1, further comprising a biasing element coupled to the flexible band and adapted to bias the flexible band to a maximum diameter.

10. A method for remotely adjusting a gastric band disposed around a stomach, comprising:
    selectively delivering energy to an electroactive polymer locking actuator disposed on a gastric band positioned around a stomach to allow slidable movement of first and second ends of the gastric band relative to one another; and
    selectively delivering energy to an electroactive polymer traversing actuator to move the first and second ends relative to one another and thereby change a diameter of the gastric band.

11. The method of claim 10, wherein the first end includes a plurality of teeth formed thereon, and the second end includes a latch mechanism formed thereon and having an opening for receiving the first end, and an arm for engaging at least one of the plurality of teeth.

12. The method of claim 11, wherein the locking actuator expands the opening when energy is delivered thereto to disengage the first end, and contracts the opening when energy delivery is terminated to engage the first end.

13. The method of claim 11, wherein the traversing actuator expands the arm when energy is delivered thereto to engage an adjacent tooth, and contracts the arm when energy delivery is terminated to move the first and second ends relative to one another.

14. The method of claim 10, wherein energy is delivered remotely to a subcutaneous transformer that is coupled to the electrically expandable and contractible actuator.

15. A method for remotely adjusting a gastric band disposed around a stomach, comprising:
    selectively delivering energy to a first electrically expandable and contractible electroactive polymer actuator disposed on a gastric band positioned around a stomach to increase a diameter of the gastric band, and selectively delivering energy to a second electrically expandable and contractible electroactive polymer actuator on the gastric band to decrease the diameter of the gastric band, wherein the first and second electrically expandable and contractible electroactive polymer actuators form at least a portion of a latch coupled to first and seconds ends of the gastric band and effective to move the first and second ends of the gastric band relative to one another.

16. The method of claim 15, wherein the second electrically expandable and contractible electroactive polymer actuator is coupled to an arm that moves the first and second ends of the gastric band relative to one another to decrease the diameter of the gastric band.

* * * * *